United States Patent [19]

Flugstad

[11] Patent Number: 5,443,490
[45] Date of Patent: Aug. 22, 1995

[54] DEFIBRILLATOR PATIENT CIRCUIT

[75] Inventor: Benjamin A. Flugstad, McMinnville, Oreg.

[73] Assignee: Hewlett Packard Corporation, Palo Alto, Calif.

[21] Appl. No.: 25,011

[22] Filed: Mar. 2, 1993

[51] Int. Cl.⁶ .............................................. A61N 1/32
[52] U.S. Cl. ....................................................... 607/5
[58] Field of Search ................................ 607/4, 5, 6, 7

[56] References Cited

FOREIGN PATENT DOCUMENTS

| 0487776 | 6/1992 | European Pat. Off. | 607/5 |
| 2931112 | 2/1981 | Germany | 607/5 |
| 9316757 | 9/1993 | WIPO | 607/4 |

*Primary Examiner*—William E. Kamm
*Assistant Examiner*—Marianne Parker
*Attorney, Agent, or Firm*—Curtis G. Rose; Brent F. Logan

[57] ABSTRACT

A defibrillator patient circuit including a capacitor having a two terminals; a first relay having a common terminal, and two contact terminals, where the first relay's common terminal is connected to the capacitor's first terminal; a charger circuit having two terminals, where the charger circuit's first terminal is connected to the first relay's first contact terminal and where the charger circuit's second terminal is connected to the capacitor's second terminal; a second relay having a common terminal, and two contact terminals, where the relay's second contact terminal is connected to the capacitor's second terminal; a first defibrillation contact connected to the second relay's common terminal; a second defibrillation contact connected to the first relay's second switch contact; and an inductor connected in series with the capacitor, the two relays, and the two defibrillation contacts.

10 Claims, 4 Drawing Sheets

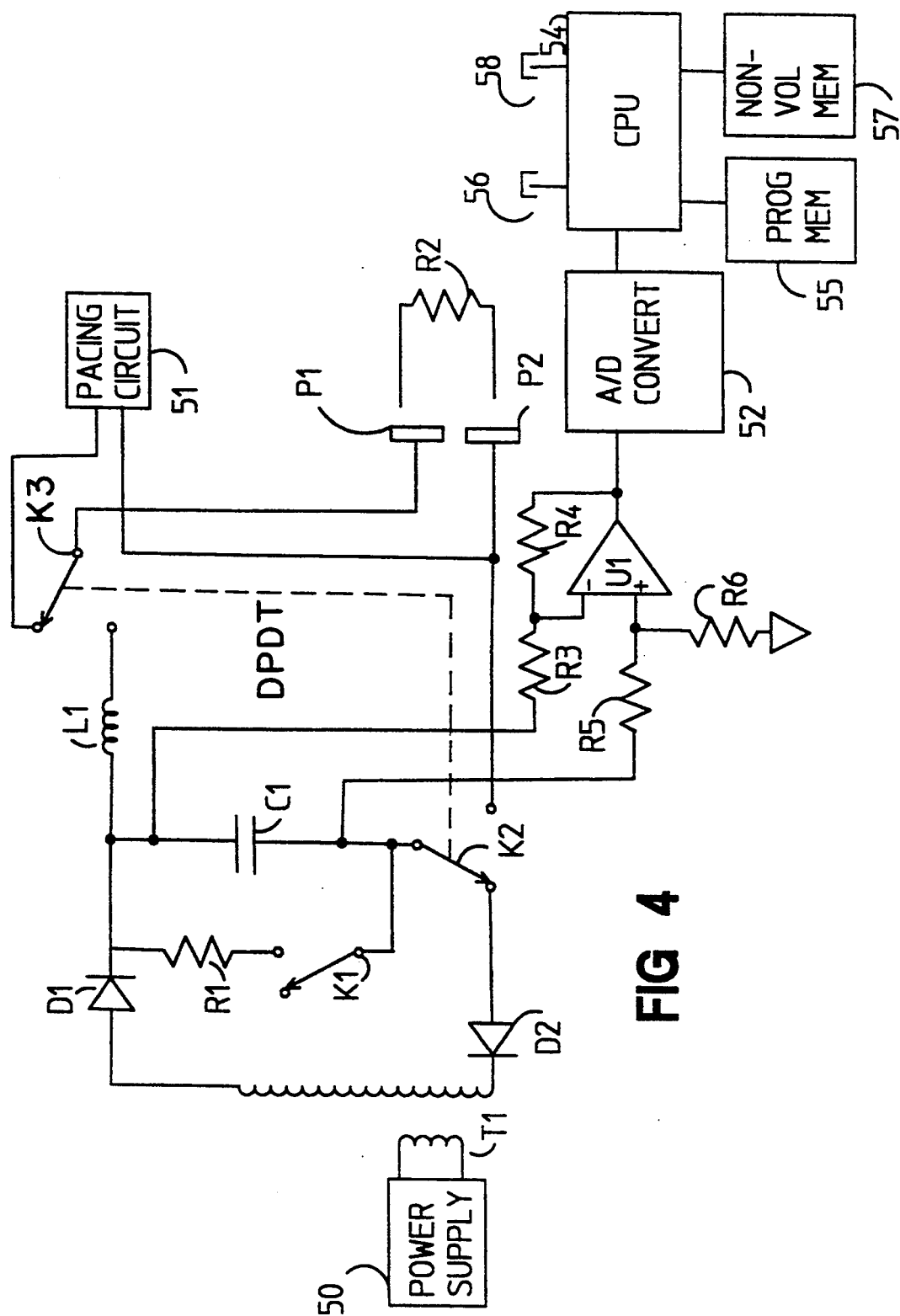

DEFIBRILLATOR PATIENT CIRCUIT

BACKGROUND

The primary function of a defibrillator is to provide a high-energy electrical pulse to a patient's heart. As such, a defibrillator will typically have a high-voltage charger, a storage capacitor, and a pair of defibrillation contacts. A plurality of switching elements, commonly being mechanical relays, alternately connect the storage capacitor to the high-voltage charger and the defibrillation contacts. During discharge, the patient must be isolated from the high-voltage charger circuit. To prevent the storage capacitor from accumulating a charge, a safety resistor can be placed in parallel with the storage capacitor.

A defibrillator may have a "pacing" circuit that periodically provides small current pulses to the patient's heart. The pacing circuit uses the same defibrillation contacts as are used for defibrillation. However, during discharge the pacing circuitry must be disconnected from the defibrillation contacts or it can be destroyed.

A first prior art patient circuit configuration is shown in FIG. 1. A pulsed-DC power supply 10 provides energy to a storage capacitor 13 through a step-up transformer 11. A diode 12 prevents the charge accumulated on the storage capacitor from dissipating. To discharge the accumulated energy to the patient, modeled in the drawing as a resistor 18, the double-pole relay 14a, 14b is switched. An inductor 15 regulates the current flow to the defibrillation contacts 16 and 17 and the patient 18.

Although functional, the patient circuit shown in FIG. 1 has some potential problems. First, if the series RLC circuit comprising the storage capacitor 13, the inductor 15, and the patient 18 is underdamped (a condition which is dependent on the patient's transthoracic impedance), then the voltage across the capacitor can go negative, forward biasing the diode 12. This "undershoot" condition" can impose a high voltage across the secondary of the step-up transformer 11 with only a small series resistance in the circuit, destroying the transformer secondary.

Second, if a pacer circuit (not shown) is connected to the defibrillation contacts 16 and 17, an additional relay is needed to protect the pacer circuit during discharge.

Third, if the relays 14a and 14b are switched from their discharge positions while current is still flowing through the inductor 15, the relays can "arc over." Because of the physical arrangement of the relays 14a and 14b in a double-pole double-throw configuration, the arc-over effectively shorts the terminals of the storage capacitor 13, destroying it.

A second prior art patient circuit configuration is shown in FIG. 2. As in FIG. 1, pulsed-DC power supply 20 provides energy to a storage capacitor 23 through a step-up transformer 21. A diode 22 prevents the charge accumulated on the storage capacitor from dissipating. To discharge the accumulated energy to the patient 28, the double-pole relay 24a, 24b is switched. An inductor 25 regulates the current flow to the defibrillation contacts 26 and 27 and the patient (modeled by a resistor 28).

This configuration for a defibrillator patient circuit shares many of the potential problems as that shown in FIG. 1. For example, it is susceptible to an arc-over condition destroying the storage capacitor 23. Also, an additional relay would be required to isolate a pacer circuit (not shown) during discharge.

The arrangement of the relays in FIG. 2 does protect the secondary of the transformer 21 from an undershoot condition.

A third prior art patient circuit configuration for a defibrillator is shown in FIG. 3. As in the prior two figures, a pulsed-DC power supply 30 provides energy to a storage capacitor 33 through a step-up transformer 31. A diode 32 prevents the charge accumulated on the storage capacitor from dissipating. To discharge the accumulated energy to the patient, modeled in the drawing as a resistor 38, the double-pole relay 34a, 34b is switched. An inductor 35 regulates the current flow to the defibrillation contacts 36 and 37 and the patient (modeled by a resistor 38).

This configuration shares the problems experienced with the patient circuit configuration shown in FIG. 2. However, the inductor's position between the relays 34a and 34b protects the storage capacitor 33 in an "arc-over" condition.

For the foregoing reasons, there is a need for a patient circuit configuration which (1) isolates the patient from the high-voltage charger circuit; (2) isolates a pacer from the storage capacitor during discharge; (3) isolates the high-voltage charger circuit from the storage capacitor during discharge; (4) minimizes the risk of relay failure due to interruption of discharge; while (5) minimizing the number of relays used.

SUMMARY

The present invention is directed to a configuration of a defibrillator patient circuit and a method of operating a patient circuit that satisfy this need.

According to the invention, the patient circuit includes a capacitor having a two terminals and a first relay having a common terminal, and two contact terminals. The first relay's common terminal is connected to the capacitor's first terminal. The patient circuit includes a high-voltage charger circuit having two terminals, with the charger circuit's first terminal connected to the first relay's first contact terminal and with the charger circuit's second terminal connected to the capacitor's second terminal. The patient circuit also includes a second relay having a common terminal, and two contact terminals, where the relay's second contact terminal is connected to the capacitor's second terminal. A first defibrillation contact is connected to the second relay's common terminal and a second defibrillation contact is connected to the first relay's second switch contact. An inductor is connected in series with the capacitor, the two relays, and the two defibrillation contacts.

Preferably, the capacitor's second terminal is connected to the second relay's second contact terminal through the inductor.

The defibrillation patient circuit preferably includes a pacer circuit which has two terminals. The pacer circuit's first terminal is connected to the second relay's first contact terminal while the pacer circuit's second terminal is connected to the first relays second contact terminal.

Because of the configuration of the patient circuit according to the present invention, certain advantages result. The patient is isolated from the high-voltage charger at all times. Because the secondary of the step-up transformer is not earth grounded, at least two components must fail before a ground loop including the patient can exist. Furthermore, the secondary of the step-up transformer is isolated from the storage capacitor during discharge, preventing the transformer from being destroyed during an "undershoot" condition. Also, the inductor prevents an "arc-over" condition from shorting the capacitor.

The invention provides a method of operating a defibrillator which has a capacitor, a safety resistor and a safety relay. The safety resistor and the safety relay are connected in series with each other and in parallel with the capacitor. The defibrillator also includes two defibrillation contacts and switches for alternately connecting and disconnecting the defibrillation contacts with the capacitor.

As a first step, the capacitor is charged while being disconnected from the defibrillation contacts and with the safety relay open. Simultaneously, the two defibrillation contacts are connected to the capacitor using the switches and the safety relay is closed. This method ensures that the safety relay is closed after the discharge is completed, even though some malfunction may have occurred as a result of the discharge.

These and other features, aspects, and advantages of the present invention will become better understood with reference to the following description and appended claims.

DESCRIPTION OF THE DRAWINGS

FIG. 4 shows a preferred embodiment of a defibrillator patient circuit.

DESCRIPTION

Figure 1:
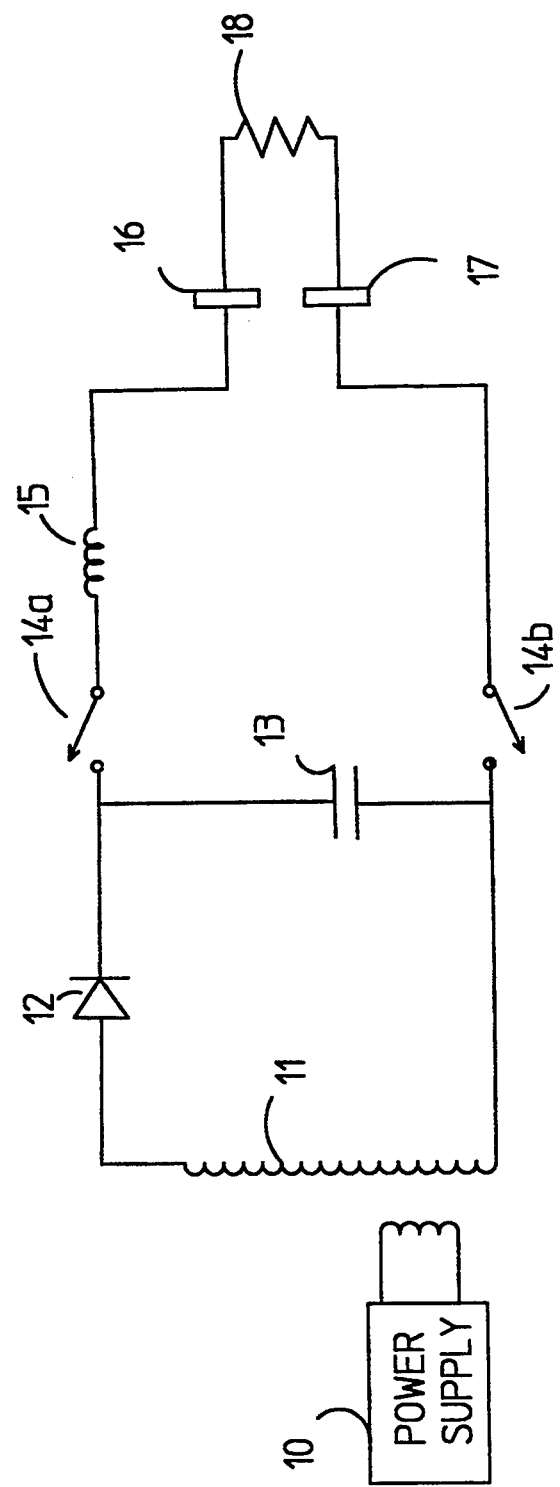
FIGS. 1–3 show prior art configurations of defibrillator patient circuits.
Figure 2:
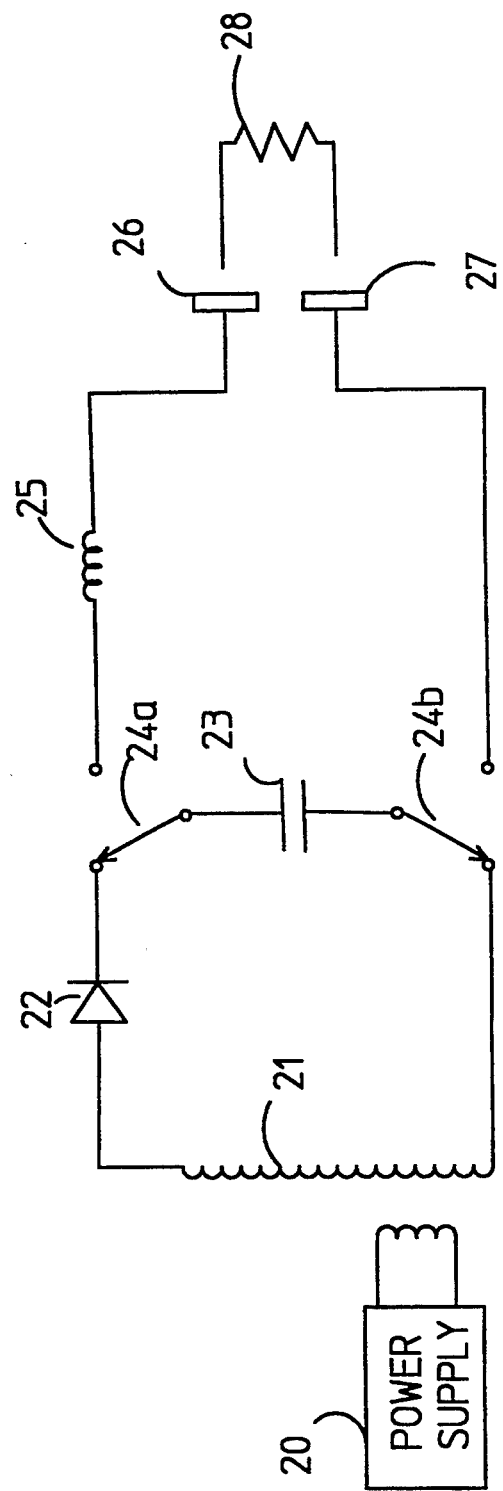
Figure 3:
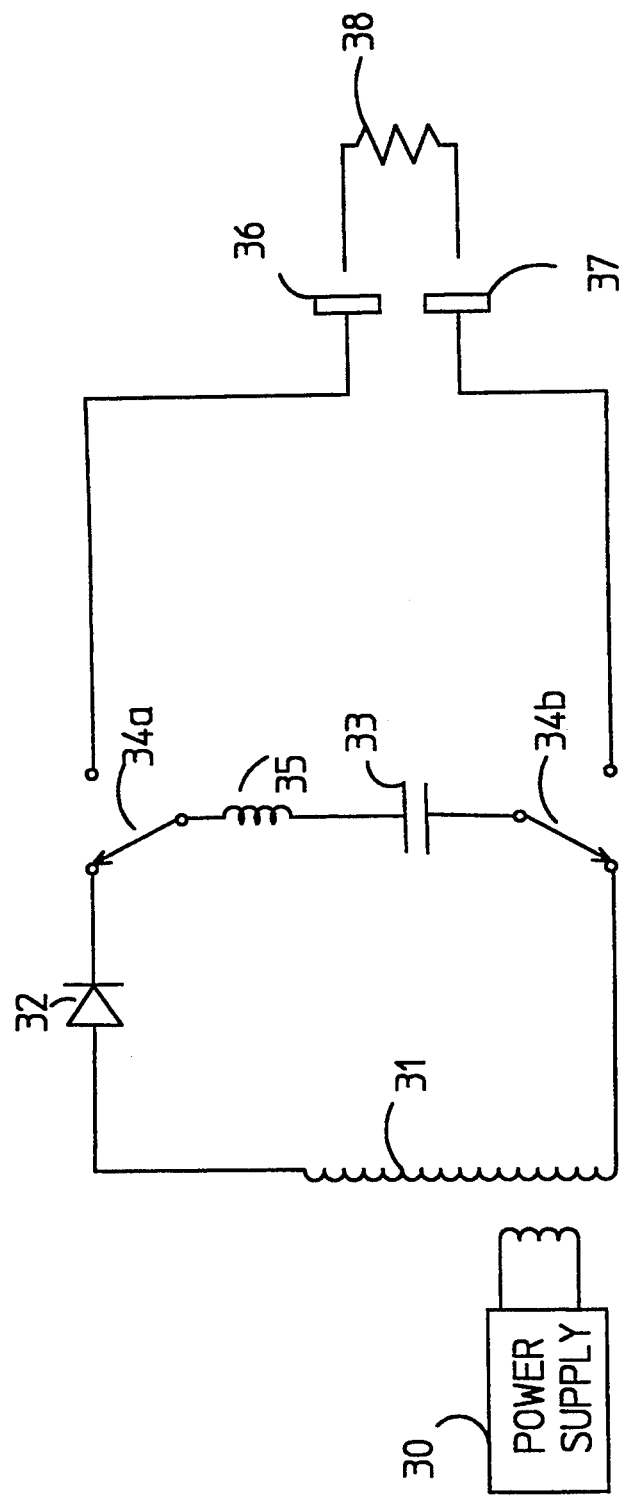

Referring now to the drawings, a preferred embodiment of a defibrillator patient circuit configuration according to the present invention is shown in FIG. 4. The primary coils of a transformer T1 connect to a pulsed-DC power supply 50. For a more detailed description of a pulsed-DC power supply, refer to a co-pending application Ser. No. 08/001,019 filed Jan. 6, 1993, entitled "Improved Dual Voltage Power Supply," which is hereby incorporated by reference. The secondary coils of the transformer connect across a high-voltage storage capacitor C1 through two diodes D1 and D2 and a double-throw relay K2. The arrangement of the diodes allows a high voltage charge to be accumulated on the storage capacitor when the power supply is activated. Preferably, the storage capacitor has a capacitance of 35 micro-Farads.

A safety resistor R1 and a safety relay K1, connected in series across the storage capacitor C1, allow the storage capacitor to be "disarmed" through the safety resistor R1. The safety resistor R1 preferably has a resistance of 47 kilo-Ohms and a power rating of 10 Watts. The safety relay K1 preferably is of the "normally closed" type, thus creating the default situation of preventing the storage capacitor from accumulating a charge.

A pacer circuit 51 is connected to the first defibrillation paddle P1 through the second double-throw relay K3 and to the second defibrillation paddle P1.

In FIG. 4, the first and second patient relays K2 and K3 are shown in their "charge" positions, which are their "normally connected" positions. Preferably, patient relays K2 and K3 together form a double-pole double-throw relay. If semiconductor switching circuits are used for the patient relays K2 and K3 in place of a double-pole double-throw mechanical relay, then preferably their drives are synchronized.

The energy accumulated by the storage capacitor C1 may be discharged into the patient (modeled in FIG. 4 by a resistor R2) through an inductor L1 and defibrillation paddles P1 and P2. The inductor preferably has an inductance of 50 milli-Henries and a resistance of 11 ohms. The patient's transthoracic resistance is typically within the range of 20 to 100 Ohms.

Discharge occurs when the patient relays K2 and K3 are moved to the positions opposite the positions they are shown in FIG. 4. In the discharge position, the pacer circuit 51 is isolated from the storage capacitor because the second patient relay K3 disconnects the pacer circuit from the first defibrillation paddle P1.

Four resistors R3, R4, R5, and R6 and an operational amplifier U1 form an instrumentation amplifier 8. The instrumentation amplifier has as its input the voltage across the storage capacitor C1. The output of the instrumentation amplifier 8 is supplied to an analog-to-digital (A/D) converter 52. The digital output of the A/D converter is provided to a microprocessor 54.

The microprocessor 54 executes program instructions contained in a program memory 55 and uses data stored in a nonvolatile memory 57. In executing the program instructions, the microprocessor controls the operation of the defibrillator, including the positions of the safety relay K1 and the patient relays K2, and K3 and the activation of the power supply 50.

The microprocessor 54 accepts input from two switches: a "charge" switch 56 and a "discharge" switch 58. Through these switches, the operator commands the microprocessor to prepare the defibrillator for use and to discharge the storage capacitor C1 to the paddles P1 and P2.

During normal operation of the defibrillator, an operator activates the "arming" switch 56. In response, the microprocessor 54 activates the power supply 50. The relays K1, K2, and K3 would already be in the positions shown in FIG. 4. The microprocessor then monitors the output of the A/D converter 52 until the storage capacitor C1 has a voltage corresponding to the desired discharge energy. At that time, the microprocessor deactivates the power supply and alerts the operator that the defibrillator is ready for discharge.

When the operator activates the "discharge" switch 58 (typically a pair of switches, one on each paddle), the microprocessor 54 moves the patient relays K2 and K3 to cause the storage capacitor C1 to discharge through the patient R2. After approximately 300 milliseconds, the microprocessor returns the patient relays K2 and K3 to the positions shown in FIG. 4. Safety relay K1 preferably is closed concurrently with discharge.

Also, the present invention provides a method of operating the defibrillator. As a first step, the storage capacitor C1 is charged as described above. Then, simultaneously, the two defibrillation contacts are connected to the capacitor using the switches and the safety relay is closed.

What is claimed is:
1. A defibrillator patient circuit, comprising:
   a capacitor having a first terminal and a second terminal;
   a first double-throw relay having a common terminal, a first contact terminal, and a second contact terminal, where the common terminal of the first double-throw relay is connected to the first terminal of the capacitor;

a high-voltage charger circuit having a first terminal and a second terminal, where the first terminal of the charger circuit is connected to the first contact terminal of the first double-throw relay and where the second terminal of the charger circuit is connected to the second terminal of the capacitor;

a second double-throw relay having a common terminal, a first contact terminal, and a second contact terminal;

a first defibrillation contact connected to the common terminal of the second double-throw relay;

a second defibrillation contact connected to the second contact terminal of the first double-throw relay; and an inductor connected to the second contact terminal of the second double-throw relay and to the second terminal of the capacitor.

2. The defibrillation patient circuit of claim 1, further comprising a safety resistor and a safety relay, where the safety resistor and safety relay are connected in series with each other and in parallel with the capacitor.

3. The defibrillation patient circuit of claim 1, wherein at least one of the double-throw relays is a mechanical relay.

4. The defibrillation patient circuit of claim 1, wherein the first double-throw relay and the second double-throw relay compose a double-pole, double-throw relay.

5. The defibrillation patient circuit of claim 4, wherein the first double-throw relay and the second double-throw relay compose a double-pole double-throw relay.

6. A defibrillator and pacing patient circuit, comprising:

a capacitor having a first terminal and a second terminal;

a first double-throw relay having a common terminal, a first contact terminal, and a second contact terminal, where the common terminal of the first double-throw relay is connected to the first terminal of the capacitor;

a high-voltage charger circuit having a first terminal and a second terminal, where the first terminal of the charger circuit is connected to the first contact terminal of the first double-throw relay and where the second terminal of the charger circuit is connected to the second terminal of the capacitor;

a second double-throw relay having a common terminal, a first contact terminal, and a second contact terminal;

a first defibrillation contact connected to the common terminal of the second double-throw relay;

a second defibrillation contact connected to the second contact terminal of the first double-throw relay;

an inductor connected to the second contact terminal of the second double-throw relay and to the second terminal of the capacitor; and a pacer circuit having a first terminal and a second terminal, where the first terminal of the pacer circuit is connected to the second terminal of the first double-throw relay, and where the second terminal of the pacer circuit is connected to the first contact terminal of the second double-throw relay.

7. The defibrillation patient circuit of claim 6, further comprising a safety resistor and a safety relay, where the safety resistor and the safety relay are connected in series with each other and in parallel with the capacitor.

8. The defibrillation patient circuit of claim 6, wherein at least one of the double-throw relays is a mechanical relay.

9. The defibrillation patient circuit of claim 6 wherein the first double-throw relay and the second double-throw relay compose a double-pole double-throw relay.

10. A method of operating a defibrillator having a capacitor, a safety resistor and a safety relay, where the safety resistor and the safety relay are connected in series with each other and in parallel with the capacitor, two defibrillation contacts, and switch means for alternately connecting and disconnecting the defibrillation contacts with the capacitor, the method comprising the steps of:

charging the capacitor with the capacitor disconnected from the defibrillation contacts and the safety relay open;

connecting the two defibrillation contacts with the capacitor using the switch means; and closing the safety relay simultaneously with said connecting step.

* * * * *